United States Patent [19]

Kelly

[11] 4,294,105

[45] Oct. 13, 1981

[54] MASS SENSING ELEMENT

[75] Inventor: Arnold J. Kelly, Princeton Junction, N.J.

[73] Assignee: Exxon Research & Engineering Co., Florham Park, N.J.

[21] Appl. No.: 138,412

[22] Filed: Apr. 8, 1980

[51] Int. Cl.³ .......................................... G01N 22/00
[52] U.S. Cl. .................................. 73/28; 177/210 FP
[58] Field of Search .......... 73/170 R, 28, 12, 432 PS, 73/580; 324/71 CP; 209/45; 310/327, 338; 177/210 FP, DIG. 11

[56] References Cited

U.S. PATENT DOCUMENTS

| 3,266,291 | 8/1966 | King, Jr. | 73/23 |
| 3,653,253 | 4/1972 | Olin | 73/28 |
| 3,715,911 | 5/1970 | Chuan | 73/28 |

Primary Examiner—Jerry W. Myracle
Attorney, Agent, or Firm—Robert S. Salzman

[57] ABSTRACT

A particle mass sensing element comprises a piezoelectric crystal, a portion of whose surface is coated with a mat-like mass of substantially rigid whiskers for entrapping or otherwise retaining particles while the crystal is caused to vibrate.

26 Claims, 6 Drawing Figures

FIG. 1
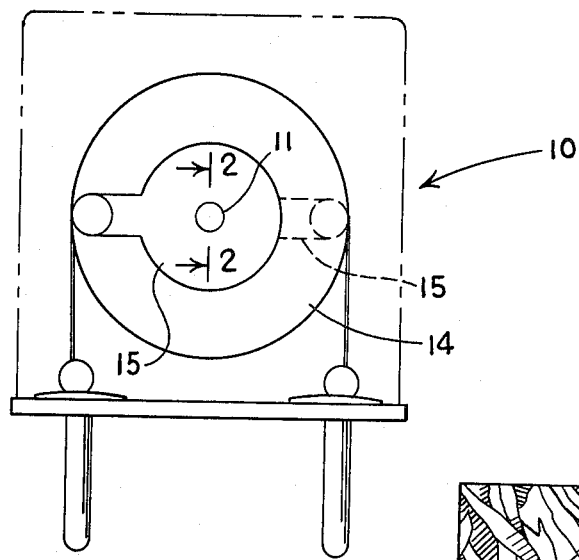
FIG. 3
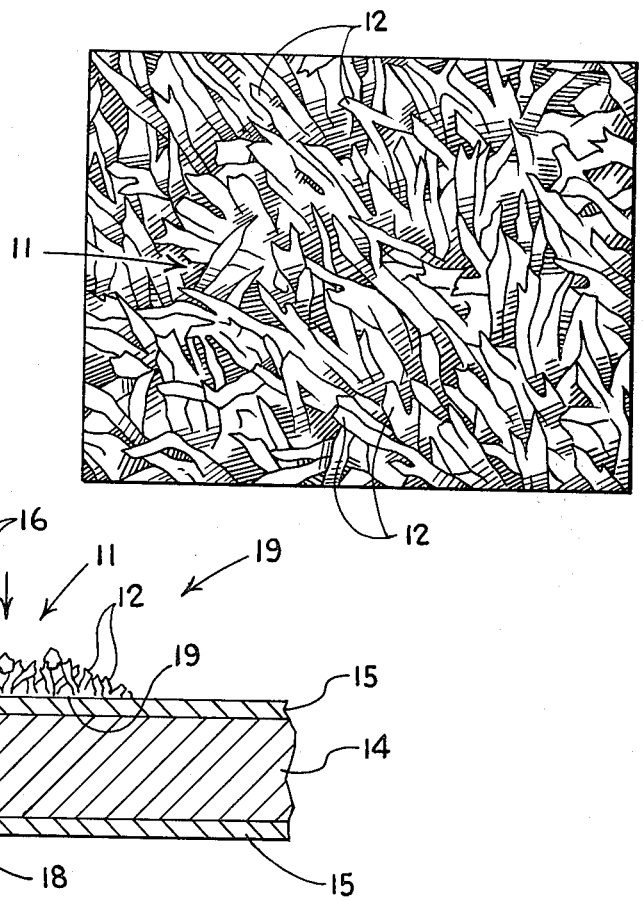
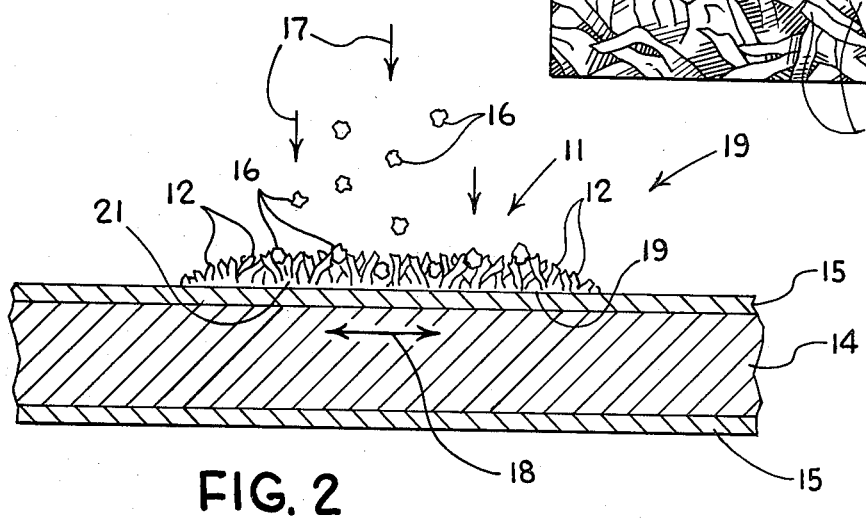
FIG. 2

TELLURIUM DENDRITE DEPOSITION

MASS SENSING ELEMENT

FIELD OF THE INVENTION

This invention pertains to the mass sensing of particles and more particularly to an improved particle mass sensing element.

BACKGROUND OF THE INVENTION AND DISCUSSION OF THE PRIOR ART

The measurement or sensing of the mass of air-borne particles and particulate materials by means of a quartz (piezoelectric) crystal micro balance is well known in the art. The piezoelectric crystal is forced to vibrate, while the particles being sensed are caused to impinge upon the vibrating crystal surface. The particles are captured by the crystal, and the vibrating frequency of the crystal is caused to decrease as a result of their capture. The mass of the collected particles which is proportional to this frequency change, is then easily measured.

One of the problems with obtaining accurate measurements of the particle mass, however, is the "positive" capture or collection by the crystal of the air-borne particles. In order to provide a proper particle-captive surface for the vibrating crystal, the crystal has in the past been coated with tacky or adhesive substances, such as silicon oil and grease-like substances. The object of these tacky coatings is to rigidly couple or adhere the impinging particles to the crystal surface, so that they can sufficiently follow the movement of the crystal surface. When this condition is achieved, the "slaved" particles will alter the oscillation of the vibrating crystal. Such a teaching can be found in the art with reference to the U.S. patents to: R. L. Chuan, entitled: Apparatus for Sensing Air-borne Particulate Matter; U.S. Pat. No. 3,715,911; issued: May 11, 1970; and W. H. King, Jr., entitled: Piezocrystal Fluid Analyzer; U.S. Pat. No. 3,266,291; issued: Aug. 16, 1966.

Tacky layers will usually provide the necessary adhesiveness to capture impinging particles, but have been found to give erroneous results. This is probably due to the fact that tacky materials are often too soft to rigidly couple the captured particles to the surface of the crystal, such that they follow the crystal movement and influence or alter the oscillations. If made more rigid so as to slave the particles to the crystal movement, these layers will not properly collect or capture the particles, such that the use of tacky layers can never be designed to be entirely successful.

Other problems with these tacky layers exist which further discourage their use. Such layers are designed to be thin so as to reduce layer shearing and crystal damping effects. When these layers are made thin, however, they are too thin to "positively" capture the incident particles; i.e., to hydrodynamically stagnate the impinging particles.

The invention is concerned with providing a surface for a mass-sensing piezoelectric crystal which will "positively" capture incident particles, such that: (1) they will not bounce when they impinge; and (2) their mass will be rigidly coupled to the oscillating crystal surface.

BRIEF SUMMARY OF THE INVENTION

The subject invention relates to an apparatus for sensing the mass of incident particles impinging thereupon. The inventive apparatus comprises a piezoelectric crystal which is coated over at least a portion thereof with a plurality of substantially rigid whiskers. The whiskers are arranged upon the crystal surface with a generally perpendicular attitude so as to form a mat-like mass. The mat-like mass will entrap or otherwise retain the incident particles while the piezoelectric crystal is caused to vibrate, and will meet the requirements generally set forth above.

For the purposes of this invention, the terms "whiskers" or "mat-like mass" are defined herein as substantially rigid fibers, hairs, dendrites, protuberances, or projections, which emanate or otherwise radially project from the surface of the crystal in a substantially perpendicular manner, but which can be screwed or twisted, and which possess the proper attitude, width and/or thickness, height, and spacing from each other so as to form a captive surface or mass for incident particles consistent with the requirements and objects of the invention set forth herein and generally known to the art.

The whiskers of the mat-like mass will have the necessary rigidity, spacing, height, width and/or thickness, and attitude required to capture particles of different or similar sizes and/or masses depending upon the analyzing objectives of the experimenter consistent with the overall mass-sensing objective. Particles or particulate matter which can be sensed by the subject inventive mat-like mass covered crystal can be either in the micron or submicron range of sizes.

The whiskers can be designed to generally have a mean spacing of approximately 5 average collected particle diameters (ACPD); a mean height of approximately 10 ACPD; and a mean width of 1 ACPD.

To provide a crystal having the proper sensitivity, the mat-like mass is generally deposited in the center or mid-portion of the crystal.

It is an object of this invention to provide an improved mass-sensing apparatus;

It is another object of the invention to provide a surface coating for a piezoelectric crystal which will positively capture incident particles or particulate materials;

It is a further object of this invention to provide a surface upon a vibrating crystal which will capture impinging particles without bounce, and which will rigidly couple the particles to the crystal.

These and other objects of the invention will become more apparent and will be better understood with reference to the following detailed description considered in conjunction with the accompanying drawings.

BRIEF DESCRIPTION OF THE DRAWINGS

FIG. 1 shows an enlarged front view of the apparatus of this invention;

FIG. 2 illustrates a further enlarged cross-sectional view of the inventive apparatus in FIG. 1 taken along lines 2—2, and depicted in situ;

FIG. 3 shows a greatly enlarged (microscopic) perspective view of the surface of the particle capture coating of the inventive apparatus of FIGS. 1 and 2;

DETAILED DESCRIPTION OF THE INVENTION

Figure 5:
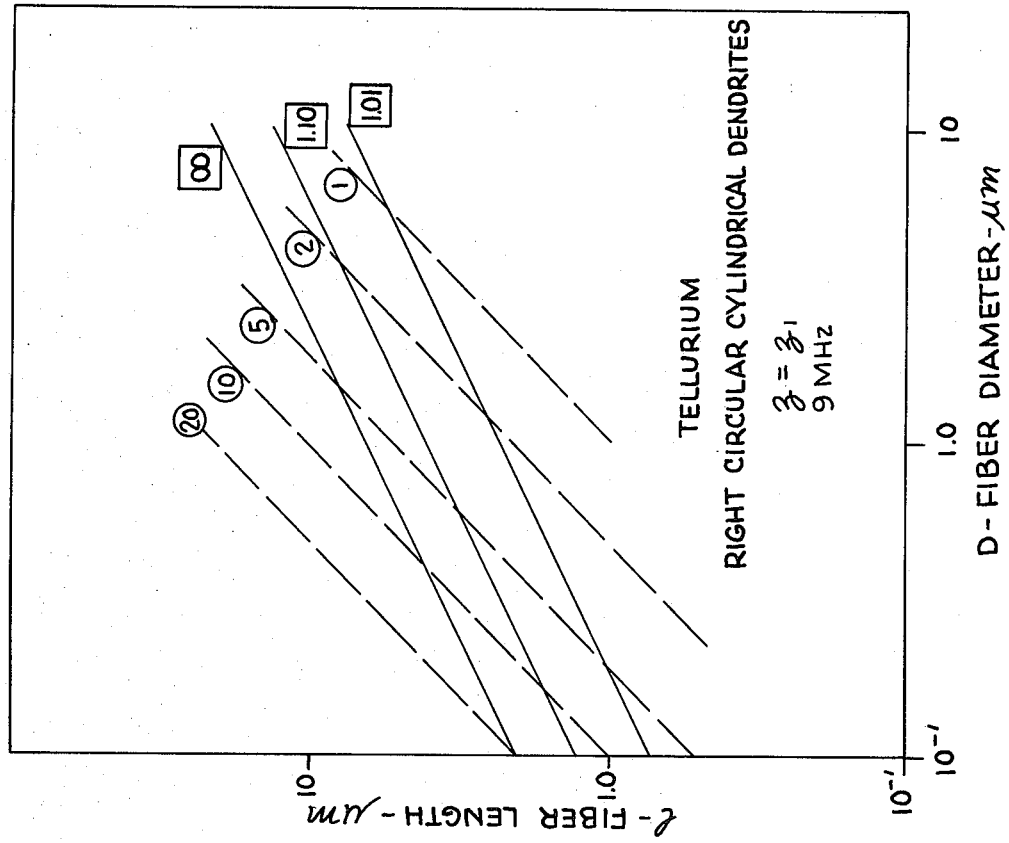
FIG. 5 illustrates in more specific graphical form the limiting lengths and diameters for the tellurium whiskers of FIG. 4 for given "mass" values.

Generally speaking, the inventive features coating a piezoelectric crystal microbalance with micron sized rigid fibers or whiskers as a means of collecting and sensing the mass of micron and submicron sized particulate.

The resulting apparatus is useful (including other uses) in monitoring or otherwise measuring the mass flux of micron sized particles in a beam or directed emission.

The piezoelectric crystal 10 of the invention is shown in an enlarged view in FIG. 1. The crystal 10 is generally coated at a mid-portion thereof with a firmly adhering rigid mass 11, which is comprised of a mat-like mass of thousands of particle-capturing whiskers 12 shown in greater detail in the further enlarged sectional view of FIG. 2 and in still greater detail in the microscopic view of FIG. 3. The commercially available crystal 10 is generally quite rugged and consists of a quartz disc 14 approximately 200 $\mu$m thick, 1.4 cm in diameter with coated nickel over gold electrodes 15 of approximately 1 $\mu$m thickness and some 8 mm in diameter.

FIG. 2 shows the mid-portion of crystal 10 receiving (arrows 17) various particles 16 of a particle beam. The crystal 10 is oscillated (arrows 18) at a frequency of 9 MHz. When the impinging particles 16 firmly adhere to the mat-like coating 11 the frequency will drop approximately 600 $H_z$ per $\mu$gram of collected particles.

Properly sized whiskers 12 will stagnate and retain particles 16 having velocities in an order of magnitude higher than the maximum possible from a solid surface having the same physical properties. Moreover, for any given whisker, this enhancement can be expected over a particle diameter range at a factor of approximately ten (10). The plurality of the whiskers 12 in proper configuration as will be explained in more detail hereinafter, will assure that an incident particle 16 will suffer multiple collisions and be captured. The whiskers 12 comprising the mat-like mass 11 should be oriented approximately parallel to the particles' initial velocity vector (arrows 17). This will insure that the particles will each undergo a glancing rebound and will continue toward the base 19 (FIG. 2) of the fibrous mat 11.

To provide maximum entrapment the whiskers 12 should be oriented perpendicular to the crystal base surface 19 as well as approximately parallel to each other, as aforementioned. It is desirable to arrest the motion of the particles 16 at or near the whiskers or mat-like base 21 to maximize retention of as large a mass of particulate matter as possible.

To obviate the problem of poor coupling between the particles and the vibrating crystal base 19, the whiskers 12 should be spaced about a particle diameter apart from each other to guarantee immobilization of the stagnated particles and assure mass-coupling between particles 16 and the crystal 10.

The vibratory motion (arrow 18) of crystal surface 19 is assumed to be rigidly coupled to the whisker base 21. Therefore, it is proper to define an apparent mass M*, the whisker's mass sensed by the crystal, as the ratio of the shear force at the whisker base 21 to the acceleration at that position. It is straightforward to show that the normalized apparent mass $\xi$ defined as the ratio of apparent mass M* to actual mass M can be expressed in terms of the vibration parameter Z as:

$$\xi = \frac{M^*}{M} = \frac{\text{Cosh}(z)\ \text{Sin}(z) + \text{Sinh}(z)\ \text{Cos}(z)}{z\ (1 + \text{Cos}(z)\ \text{Cosh}(z))} \quad (1)$$

* 1 nm/min (Solid Equivalent) $\approx 10^{-7}$ kg/m$^2$ sec tellurium.

The vibration parameter z is defined as:

$$z = 2 \left(\frac{\rho}{E}\right)^{\frac{1}{4}} \left(\frac{\omega l^2}{D}\right)^{\frac{1}{2}}, \text{(dimensionless)}, \quad (2)$$

where: $\rho$=density, (kg/m$^3$); E=Young's Modulus, (N/m$^2$); l,D=fiber length and diameter, (m).

In the limit of vanishing small frequency, z=o, as would be anticipated, $\xi$=1. With increasing frequency $\xi$ remains close to unity until the vicinity of the first resonance, $z_1$=1.8751, at which point $\xi \rightarrow \infty$. At frequencies slightly in excess of $z_1$, $\xi < 0$ implying negative sensed mass, the normalized mass again increasing, though zero to become infinite at the second resonant state, $z_2$=4.6941. The resonance condition $$1 + \text{Cos}\ z\ \text{Cosh} z = 0 \quad (3)$$

is identical to that of an undriven oscillator.

The presence of narrow domains of negative normalized sensed mass at frequencies slightly in excess of resonance reflects a phase shift of 180° between the force and acceleration at the whisker's base 21 as the resonance state is traversed. This is not unexpected insofar as the system is assumed to be dissipationless, the total energy being zero over a cycle of oscillation.

The potential exists for operating crystal 10 having arbitrarily long whiskers 12 attached to its surface 19 provided pertinent parameters are adjusted to satisfy one of the infinitude of possible null points ($\xi$=0). It should be noted that at sufficiently high values of z (e.g., $z \gtrsim z_{10}$) the apparent mass is strongly influenced by its inverse dependence on z. As a consequence, the apparent mass is close to zero over much of the range of z values between resonances.

Piezoelectric crystals will measure attached whisker mass quite accurately over a substantial range of z values. Operation at z values below approximately half the resonance condition, i.e., $z \lesssim \frac{1}{2} z_1$ insures that the crystal's ability to accurately measure deposited particulate matter will be virtually uninfluenced by the whisker's presence. Stiffening of the whisker by material deposited at their base 21 results in lower effective lengths, reduced values of z, and, therefore, smaller departure of the sensed mass from the true mass.

From a broader perspective, if the collction rate is sufficiently small so that whisker stiffening occurs slowly (i.e., the change in z is small over any one measuring interval) the whisker's presence can be neglected. As a rule of thumb, for operation at frequencies half or less of the first resonance, the percentage alteration of indicated mass change due to the whisker's presence will be equal to or less than the percentage of whisker length covered by the material deposited. Therefore, if the measurement interval is made sufficiently small, no consideration need be given to the effect of whisker dynamics on crystal mass sensitivity.

It must be stressed that the foregoing considerations have assumed that all incident particulate material 16 would collect and become compacted at the whisker's base 21. This is obviously a gross simplification. The more realistic situation is one where particulate matter 16 coats both the whiskers 12 and the whisker base 21. The addition of strongly adhering particulate matter to the whisker would serve to increase its flexual rigidity and increase its resonant frequency.

To avoid possible ambiguity in interpreting crystal frequency change data, operation should be restricted to below the first resonance condition $z_1 = 1.8751$. Applying this as a limiting condition, allows the maximum length and length-to-diameter ratio for vibrating whiskers to be defined.

Figure 4:
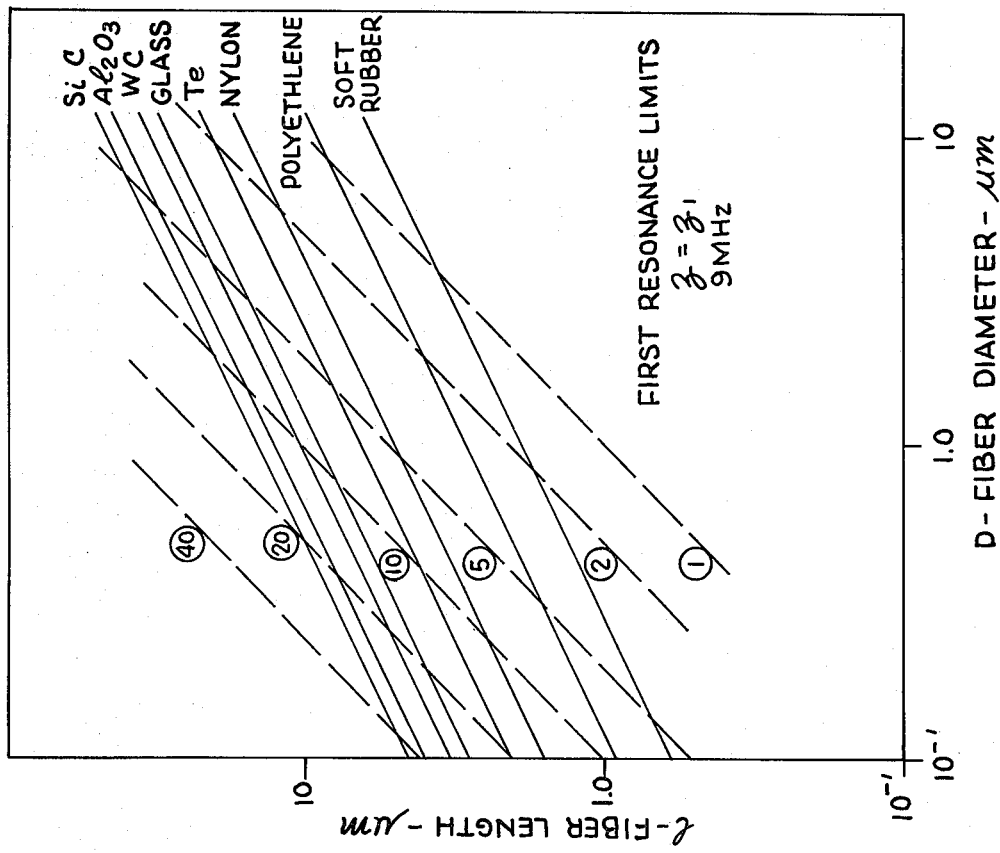
FIG. 4 depicts a graph of the maximum length and length-to-diameter ratios for vibrating whiskers for the inventive coating of FIGS. 1-3.

Referring to FIG. 4, the limiting length, diameter lines for various materials of interest oscillating at 9 MHz are displayed. The importance of high $E/\rho$ is clearly demonstrated; the lower this value the shorter and "squatter" the whisker 12 has to be and the lower the allowable length to diameter (fineness) ratio. Most candidate materials, as shown, could be used to develop sub-micron sized whiskers with length to diameter ratios of order 5 or higher, the maximum length-to-diameter ratio depending inversely on the square root of the whisker diameter.

A more realistic definition of limiting length and diameter is obtained (for tellurium whiskers) by specifying an appropriate maximum value for the parameter $\xi$. Three values for $\xi$ corresponding to divergences from unity of 1%, 10% and the resonant condition ($\xi \to \infty$) are shown plotted in FIG. 5. The important point to observe from this plot is the potential for high length to diameter ratio for tellurium whiskers possessing $\xi$ values close to unity in the useful diameter range from 0.1 to 1 $\mu$m.

For example, a half micron diameter tellurium whisker would have to be ~4 microns long to become resonant at 9 MHz. At that frequency, reducing the whisker's length to 3 microns (1D=6) results in $\xi = 1.1$, i.e., the whisker's "sensed" mass would be within 10% of its actual mass. A length-to-diameter (fineness) ratio of 6 while quite reasonable and potentially capable of fulfilling requirements for particle stagnation and capture probably represents a lower limit for operation of $\frac{1}{2}$ micron whiskers.

All calculations as presented in FIGS. 4 and 5 have been made for operation at 9 MHz. Since the frequency parameter z is a function of $\omega l^2/D$, decreasing the frequency for fixed D and z permits a commensurate increase in 1. For a $\frac{1}{2}$ micron cylindrical whisker lowering the operating frequency from 9 MHz to 3 MHz would permit operating whiskers of 5 micron length as opposed to 3 micron lengths formerly associated with $\xi = 1.1$. While crystal sensitivity is sacrificed at lower frequencies it is possible, in principle, to use as large a whisker (large fineness ratio) as defined by simply going to lower frequencies.

A tellurium whisker collection surface 11 to be used with 9 MHz piezoelectric crystal microbalances 10 for the measurement of ~0.1 to ~1.0 $\mu$m particulate matter 16 should have the following characteristics:

1. Whiskers: ~$\frac{1}{2}$ $\mu$m diameter, 3 to 5 $\mu$m long, tapered and pointed ends.
2. Morphology: whiskers skew, approximately parallel to the particle stream, approximately perpendicular to the crystal surface 19 and on the average $\frac{1}{2}$ $\mu$m to 1 $\mu$m apart at their base 21. Whisker-whisker contact desirable.
3. Mass: the total mass of coating 11 has to be insufficient to overload the crystal 10, under all circumstances (e.g., when saturated with particulate matter).

The last requirement, while not discussed heretofore, is of obvious importance. It has particular relevance when the practical problems associated with whisker surface development are considered.

To be compatible with piezoelectric crystal operation, a process for growing whiskers 12 (dendrites) directly on crystal surfaces 19, at temperatures below ~400° C., at total surface densities of less than several $\mu$g/mm$^2$, is necessary. Vapor deposited tellurium would satisfy these restrictions by virtue of its low melting point (449.5° C.), reasonable vapor pressure at low temperatures and highly anisotropic crystalline structure. In addition, tellurium's physical properties place it between nylon and glass with respect to its vibrational behavior (FIG. 4). Therefore, it should be quite representative of a wide class of industrially important materials.

Figure 6:
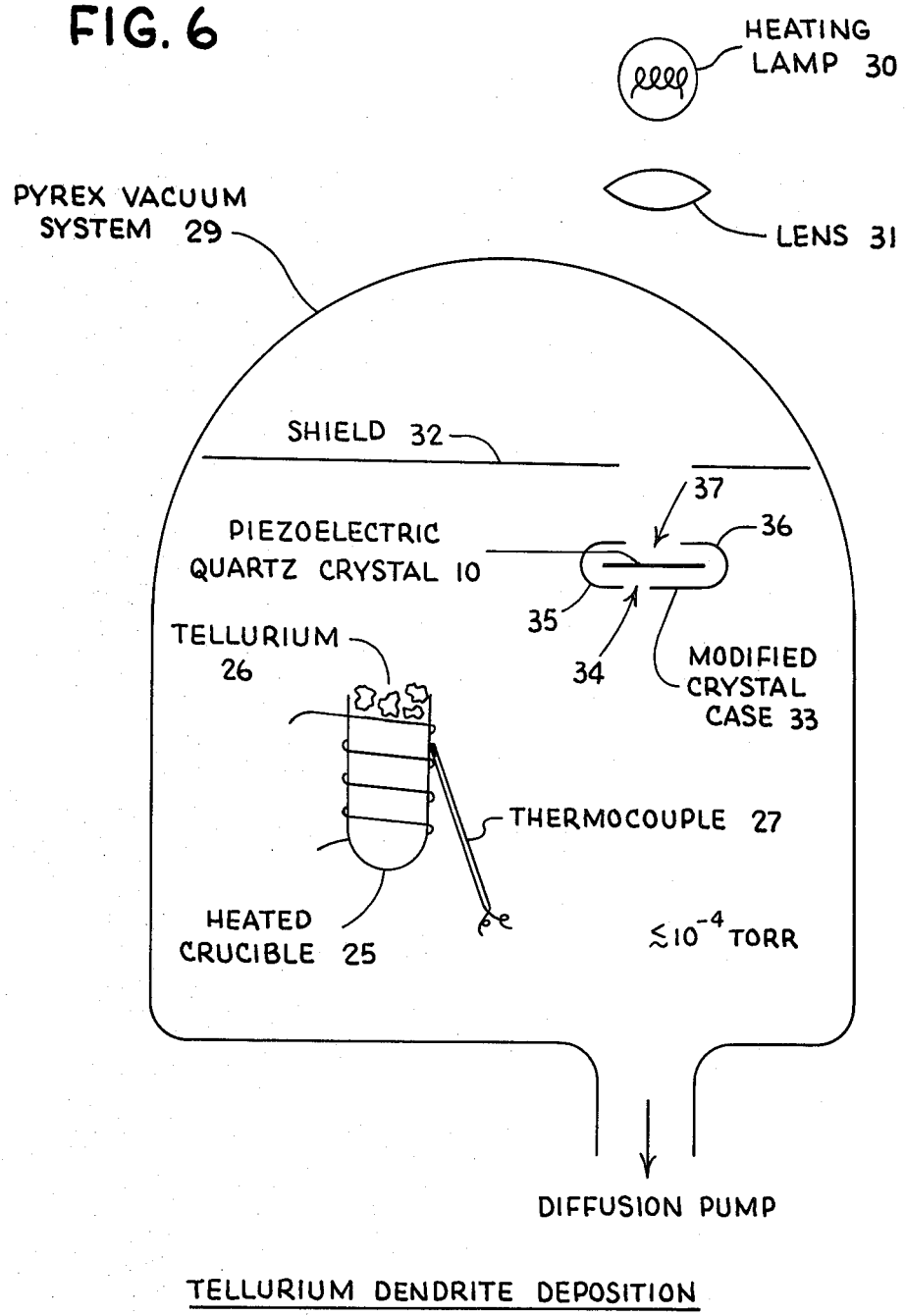
FIG. 6 shows a schematic diagram of the whisker deposition apparatus used to fabricate the inventive coating depicted in FIGS. 1-3.

The apparatus shown in FIG. 6 was assembled for deposition of the tellurium onto crystal 10. This apparatus consisted of a central, heated pyrex crucible 25 (7.5 mm ID×20 mm deep) capable of holding approximately two grams of granular tellurium 26 (tellurium splatters, 99.999+ pure ROC/RIC—Research Organic-/Inorganic Chemical Corp.), an integral thermocouple 27 to monitor crucible temperature and thereby provide information on sublimation rate, and a support structure 28 for placing piezoelectric quartz crystals 10 within a wide range of positions and orientations with respect to the central crucible. These components were contained in a pyrex vacuum system 29 capable of sustained pressures below ~$10^{-4}$ torr.

Provision was made to vibrate the crystal 10, if desired, during deposition. In addition, an external high intensity lamp 30 heated the crystal 10 via lens 31. This enhanced the deposited tellurium's surface mobility. Crystal temperature was inferred from the frequency shift observed as the crystal 10 attained its stable operative temperature.

An internal stainless steel shield 32 was employed to shadow the lower portion of the experiment from the heating lamp's output. This shield 32 also prevented vaporized tellurium from coating the upper portion of the vacuum chamber where its presence could have interfered with the heating lamp's effectiveness.

In all tests, Reeves Hoffman 6A32 crystals were used. In the main, tests were conducted with 9 MHz crystals although a number were also made with 3 MHz crystals as well. It was found convenient to modify the easily removable crystal case 33 (HC6U configuration) by the addition of an appropriately sized and positioned aperture hole 34 on the side 35 toward the tellurium crucible. In this way reproducibility of deposition spot size and position could be assured. The reverse side 36 of the crystal case 33 was opened with a 12 mm diameter hole 37. This assisted venting of the case 33 and, more importantly, permitted the radiation from the heater lamp 30 (GE Model DMK Projector Lamp) to be focused directly on the crystal 10.

Dendrites were successfully grown under the following conditions:

| | |
|---|---|
| Pressure: | $\lesssim 2 \times 10^{-4}$ Torr |
| Crystal Temperature: | 105° to 120° C. |
| Deposition Rate: | 1 nm/min to 63 nm/min* |

-continued

| | |
|---|---|
| Total Surface Density: | (solid equivalent)<br>≈20 μg/mm² |

*1 nm/min (Solid Equivalent) ≈ $10^{-7}$ kg/m² sec tellurium.

In addition to the nickel plated crystal electrode surface dendrites were also developed on: aluminum oxide, brass, glass, iron, nickel-silver alloy, quartz, salt (NaCl), Scotch brand magic tape (ungummed side), silicon and stainless steel (304). Dendrites failed to develop on copper, silver, mylar and silicone oil coated surfaces. Because the tellurium dendrites are adversely affected by humidity, the dendrites are often given a thin coating of gold.

No influence on the development process could be ascribed to static electric or magnetic fields, surface roughness, surface stress level, surface crystal size, level of nickel surface oxidation or the presence or absence of oxidation of the sublimating tellurium.

Deposition was adjusted to permit dendrite growth at an angle of about 55° from the normal. The highly magnified mat-like surface 11 shown in FIG. 3, clearly shows the dendrites 12 columnar structure and their pointed ends. The following average properties were measured for this surface, and are listed in Table I below:

TABLE I

| | | |
|---|---|---|
| 1. | Dendrite length: | 2.3 ± 0.6 (μm) |
| 2. | Dendrite width: | 0.6 ± 0.3 (μm) |
| 3. | Dendrite centerline spacing: | ~1.2 (μm) |
| 4. | Dendrite mass per unit area: | ~2.2 (μg/mm²) |
| 5. | Dendrite surface equivalent density: | ~1 (gm/cm²) |
| 6. | Vibrational parameter: | ~0.5 $z_1$ |
| 7. | Maximum particle size: | ~0.8 μm |

FIG. 3 may be quite misleading in appearance insofar as the dendrites, which are magnified 3000x, are being viewed obliquely. Significant free space exists between the individual dentrites to accommodate particles up to the sizes noted.

These surfaces have low density, defined in the standard sense of mass per volume of surface considered, i.e., the ratio of dendrite surface mass density to mean dendrite height from the surface. Surface mean densities close to unit (gms/cm³) are typical of all well developed dendritic surfaces developed thus far. Tellurium's density of 6.24 (gms/cm³) implies these dendrite structures are over 80% void.

Having thus described the invention, what is desired to be protected by Letters Patent is presented in the following appended claims.

What is claimed is:

1. An apparatus used for sensing the mass of incident particles impinging thereupon, comprising a piezoelectric crystal coated over at least a surface portion thereof with a plurality of substantially rigid whiskers having a generally perpendicular attitude with respect to said crystal surface and forming a mat-like mass upon said crystal so as to entrap or otherwise retain said incident particles while said piezoelectric crystal is caused to vibrate.

2. The apparatus of claim 1, wherein said whiskers are comprised of a metal which is vacuum deposited upon a surface of said piezoelectric crystal.

3. The apparatus of claim 2, wherein said metal is comprised of tellurium.

4. The apparatus of claim 1, wherein said coated portion of said crystal is a center portion.

5. The apparatus of claim 1, wherein said whiskers are distributed upon said crystal with a mean spacing of approximately 5 average collected particle diameters.

6. The apparatus of claim 1, wherein said whiskers are distributed upon said crystal having a mean height of approximately 10 average collected particle diameters.

7. The apparatus of claim 1, wherein said whiskers are distributed upon said crystal having a mean width of approximately 1 average collected particle diameter.

8. The apparatus of claim 1, wherein said particles are micron and sub-micron sized.

9. The apparatus of claim 1, wherein said piezoelectric crystal is caused to vibrate with a surface amplitude in the range of 1 to 10 μm.

10. The apparatus of claim 1, wherein said piezoelectric crystal comprises a single quartz disc approximately 200 μm thick having nickel over gold electrodes.

11. The apparatus of claim 1, wherein said whiskers are arranged substantially parallel with respect to each other.

12. The apparatus of claim 1, wherein said whiskers have a generally parallel attitude with respect to an initial velocity vector of said impinging particles.

13. The apparatus of claim 12, wherein said whiskers are arranged substantially parallel with respect to each other.

14. The apparatus of claim 1, wherein said whiskers may be skewed about said crystal surface.

15. An apparatus used for sensing the mass of incident particles impinging thereupon, comprising a piezoelectric crystal coated over at least a surface portion thereof with a plurality of substantially rigid whiskers having a generally parallel attitude with respect to an initial velocity vector of said impinging particles and forming a mat-like mass upon said crystal so as to entrap or otherwise retain said incident particles while said piezoelectric crystal is caused to vibrate.

16. The apparatus of claim 15, wherein said whiskers are comprised of a metal which is vacuum deposited upon a surface of said piezoelectric crystal.

17. The apparatus of claim 16, wherein said metal is comprised of tellurium.

18. The apparatus of claim 15, wherein said coated portion of said crystal is a center portion.

19. The apparatus of claim 15, wherein said whiskers are distributed upon said crystal with a mean spacing of approximately 5 average collected particle diameters.

20. The apparatus of claim 15, wherein said whiskers are distributed upon said crystal having a mean height of approximately 10 average collected particle diameters.

21. The apparatus of claim 15, wherein said whiskers are distributed upon said crystal having a mean width of approximately 1 average collected particle diameter.

22. The apparatus of claim 15, wherein said particles are micron and sub-micron sized.

23. The apparatus of claim 15, wherein said piezoelectric crystal is caused to vibrate with a surface amplitude in the range of 1 to 10 μm.

24. The apparatus of claim 15, wherein said piezoelectric crystal comprises a single quartz disc approximately 200 μm thick having nickel over gold electrodes.

25. The apparatus of claim 15, wherein said whiskers are arranged substantially parallel with respect to each other.

26. The apparatus of claim 15, wherein said whiskers may be skewed about said crystal surface.

* * * * *